United States Patent
Gilan et al.

(10) Patent No.: US 9,285,315 B2
(45) Date of Patent: Mar. 15, 2016

(54) CALCULATING THE OPTICAL DENSITY OF A FLUID TRAVELING THROUGH A GAP

(75) Inventors: Ziv Gilan, Kfar-Harif (IL); Zvi Shemer, Nes Ziona (IL); Zeharia Levi, Petach Tikva (IL); Erez Lampert, Nes Ziona (IL); Niv Shemtov, Rishon LeZion (IL)

(73) Assignee: Hewlett-Packard Indigo B.V., Maastricht (NL)

( * ) Notice: Subject to any disclaimer, the term of this patent is extended or adjusted under 35 U.S.C. 154(b) by 0 days.

(21) Appl. No.: 14/376,310

(22) PCT Filed: Feb. 8, 2012

(86) PCT No.: PCT/IL2012/000070
§ 371 (c)(1),
(2), (4) Date: Aug. 1, 2014

(87) PCT Pub. No.: WO2013/118107
PCT Pub. Date: Aug. 15, 2013

(65) Prior Publication Data
US 2014/0375997 A1    Dec. 25, 2014

(51) Int. Cl.
    G01N 21/00    (2006.01)
    G01N 21/59    (2006.01)
    G01N 21/03    (2006.01)
    G01N 21/05    (2006.01)

(52) U.S. Cl.
    CPC ........ *G01N 21/5907* (2013.01); *G01N 21/0303* (2013.01); *G01N 21/05* (2013.01); *G01N 21/59* (2013.01); *G01N 2021/5969* (2013.01)

(58) Field of Classification Search
    CPC ....... G01L 1/242; G01L 1/246; G01L 11/025; G01L 19/0092; G01L 1/06; G01L 1/127; G01L 1/142; G01L 1/22; G01L 1/2287; G01L 1/243; G01L 25/00; G01L 9/0032; G01L 9/0072; G01L 9/0076; G01L 9/02
    See application file for complete search history.

(56) References Cited

U.S. PATENT DOCUMENTS

| 7,643,766 B2 | 1/2010 | Horiuchi |
| 2009/0059332 A1* | 3/2009 | DiFoggio et al. ............. 359/196 |
| 2010/0086297 A1 | 4/2010 | Nishiyama |

FOREIGN PATENT DOCUMENTS

| EP | 1010975 A1 | 6/2000 |
| JP | 5187995 A | 7/1993 |
| JP | 8219981 A | 8/1996 |
| JP | 2009014239 A | 1/2009 |

OTHER PUBLICATIONS

International Search Report and Written Opinion for PCT/IL2012/000070 dated Sep. 26, 2012, 14 pp.

* cited by examiner

*Primary Examiner* — Michael P Stafira (57) ABSTRACT

A method and apparatus to calculate the optical density of a fluid (110) traveling through a narrow gap (30) with a set width. Typically, a densitometer employs a light source (10) that is configured to transmit light across the gap and a detector, opposite the light source (10), configured to detect light transmitted from the light source, across the gap, for calculating the optical density of the fluid. The apparatus and method further include a transparent element (120), the transparent element part of a set of replaceable transparent elements, each replaceable transparent element having a particular width, the width less than the width of the gap. Typically, the transparent element is moved into the gap between the light source and the detector to narrow the effective sampling width of the gap for calculating the optical density of the fluid. In some examples, the transparent element is further configured to rotate in the gap to enhance the flow of the fluid through the gap.

17 Claims, 9 Drawing Sheets

CALCULATING THE OPTICAL DENSITY OF A FLUID TRAVELING THROUGH A GAP

BACKGROUND

Densitometers can measure the passage of light through a transparent or semitransparent material. The measured density of a measurable substance is typically determined by measuring a decrease in the amount of light which passes through the measurable substance, the measurement may be related to the absorption of light of the measurable substance.

Most densitometers include a light source, often a laser, aimed at a photoelectric cell, with the measurable substance between the light source and the photoelectric cell. The densitometer determines the density of the measurable substance by analyzing the attenuation of light from the light source that has passed through the substance, and comparing that value with a known reference value.

Densitometers can be either transmission densitometers or reflection densitometers. Transmission densitometry instruments typically measure how transparent a substance is to visible light or other electromagnetic radiation. Reflection densitometry devices measure the amount of reflected signal, typically light or other electromagnetic radiation, of a sample. Densitometers are used in many industries as tools to measure the optical density of materials, i.e., liquids, and to provide quality assurances of a particular liquid, including foodstuffs, medications, or ink for printers.

BRIEF DESCRIPTION OF THE DRAWINGS

Examples are described in the following detailed illustrated in the accompanying drawings in which.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the methods and apparatus. However, it will be understood that the present methods and apparatus may be practiced without these specific details. In other instances, well-known methods, procedures, and components have not been described in detail so as not to obscure the present methods and apparatus.

Figure 1A:
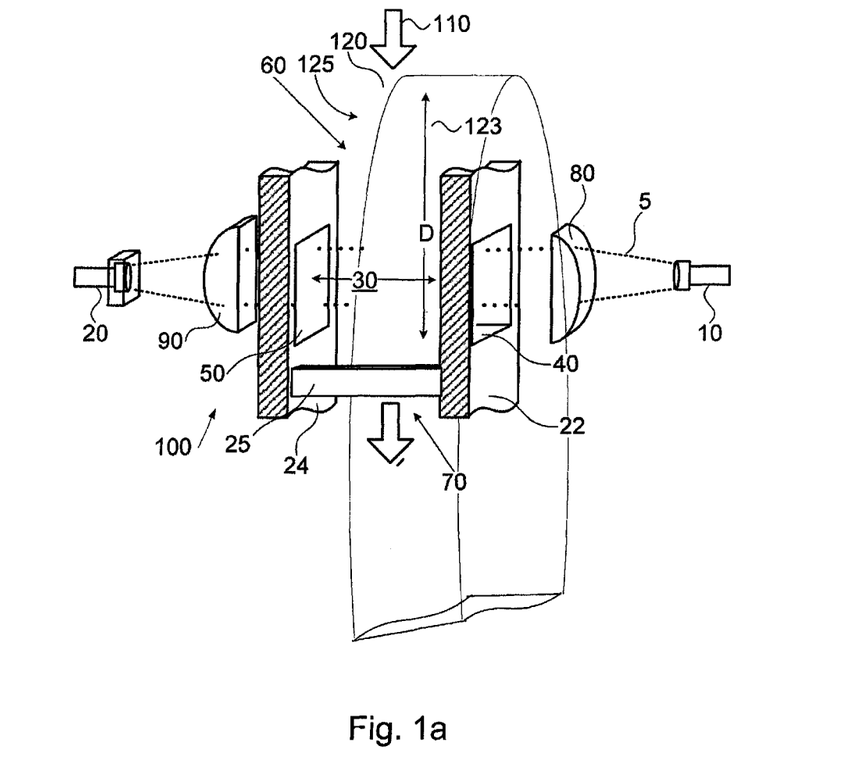
FIG. 1a is a schematic illustration of a transparent disk configured to be placed in a gap between a light source and a receiver according to one example.

FIG. 1a is schematic illustration of a densitometer 100 configured to pass light across a gap 30. In some examples, densitometer 100 is configured to measure the optical density of a fluid sample passing through gap 30. Typically, a light source 10, in some examples, a laser, is configured to be aimed towards a receiver 20 across a gap 30. Other light sources known in the art may also be used. Receiver 20 may be a photoelectric cell. Other receivers or optical sensors known in the art may also be used Densitometers typically measure light absorption through a medium, in some examples, the analysis of the transmission and absorption of the beam of light 5 from light source 10, through a fluid 110 in gap 30, to receiver 20 may provide a measurement of the optical density of the fluid that passes between light source 10 and receiver 20.

When measuring the optical density of a fluid traveling through gap 30, there may be concerns that light from light source 10 may be attenuated by the fluid in the gap, to a degree that may negatively affect the experimental results of densitometer 100. In some examples, this may be when fluid 110 has a high concentration of solid particles, and/or when fluid 110 is thick or somewhat viscous. In some examples, black ink in a printer may have a high concentration of solid particles and may be somewhat viscous.

Narrowing gap 30 may result in a lesser amount of light attenuation as it passes through fluid 110 in gap 30 on the way to receiver 20, the fluid typically attenuating light from light source 10 as light passes through to receiver 20. Typically, when gap 30 is narrowed, this may also limit the flow of a fluid through the gap, particularly when the gap is narrowed substantially.

In some examples, an element, may be introduced or moved into the gap to facilitate or enhance the flow of fluid 110, as described below with reference to a transparent disk 120. In some examples, this element may also be configured to limit the volume of fluid 110 passing through gap 30, such that less light from light source 10 is attenuated by fluid, and, in some examples, more accurate measurements of light absorbance may be obtained.

In some examples, the analysis of the transmission of beam of light 5 may provide a measurement of the absorbance of the light by fluid 110. In some examples, the analysis of changes to the transmitted beam of light 5, as it passes through fluid 110 and gap 30, may provide a measurement of the attenuation of the light from light source 5 by the fluid.

Typically beam of light 5 from light source 10 traverses a set distance from light source 10 to detector 20. In some examples, the distance is a width of gap 30.

Gap 30 typically has a width of between 300 microns to 4000. In some examples, light source 10 is configured to first diffuse the light before it passes through gap 30, by a diffuser, as is known in the art.

Gap 30 is typically defined as the space between a first window 40 and a second window 50. Window 40 and window 50 are typically made from a transparent material, such as a glass, a plastic, or other materials known in the art.

The width of gap 30 is typically determined by one spacer 25 or a plurality of spacers between the two windows. Spacer 25 is configured to maintain a predetermined distance between the first and second windows and also allow fluid 110 to pass through gap 30 between the windows. Typically, the spacer is made of one material, or a plurality of materials, the materials may include, for example, hardened steel. Typically, the materials have a high degree of tolerance to within +/−10 microns. Other materials, known in the art may also be used In some examples, gap 30 may be configured to be positioned between two walls, wall 22, which in some examples, includes window 40 and wall 24, which in some examples, includes window 50. In some examples, gap 30 maybe further configured to be positioned between an inlet 60 to allow fluid 110 in, and an outlet 70, such that the pathway that fluid 110 travels through gap 30 is perpendicular or nearly perpendicular to the pathway of beam of light 5 from light source 10. In some examples, inlet 60 is part of a pathway of ink in a printer, inlet 60 connected to an ink reservoir as described below with reference to FIG. 2. In some examples, outlet 70 is part of the pathway in a printer, the pathway ending at a printing element of a printer. In some examples, inlet 60 and outlet 70 are part of a pathway of a quality assurance system. In some examples, inlet 60 and outlet 70 are part of a pathway in a production line.

In some examples, a lens 80 is positioned between light source 10 and first window 40. In some examples, a lens 90 is positioned between second window 50 and receiver 20. Typically, lens 80 may be a collimating lens. In some examples, lens 80 is configured to collimate the light from light source 10 prior to passing through window 40. In some examples, lens 90 is a focusing lens. Lens 90 may be configured to collect the light after it has passed through gap 30 and window 50.

A densitometer 100 may include light source 10, lens 80, gap 30, lens 90 and receiver 20. In some examples, densitometer may not include lens 90 and/or lens 80.

In some examples, fluid 110 is a fluid with an expected high optical density value, i.e., with high absorption or attenuance coefficient, typically, ink, e.g., ink of between 0.05% NVS to 15% NVS, such as, for example, black ink.

Fluid 110 may be measured by densitometer 100 to assess the optical density of fluid 110 passing through gap 30 from inlet 60 toward outlet 70.

A transparent disk 120 may be configured to be placed within gap 30. Transparent disk 120 may be made from transparent plastic, glass or other known transparent materials in the art. The transparent disk may be configured to be transparent to light beam 5, i.e., transparent disk 120 may transmit light beam 5 with to minimal distortion and/or absorption, so as to allow sufficient light to pass through transparent disk 120 in order for the densitometer to determine the density of fluid 110. Typically, transparent disk 120 may be partially inserted into gap 30, so that a first and second surfaces, typically opposite surfaces, may be partially in gap 30. A surface 123 of transparent disk 120 faces window 40. A surface 125 of transparent disk 120 faces window 50.

In some examples, surface 123 and surface 125 have diameters D of between 20 mm and 100 millimeters.

FIG. 1a is an exemplary depiction of a transparent disk 120 in gap 30. Typically, diameter D is greater than the height of gap 30, wherein only a fraction of transparent disk 120 may be in gap 30 at any point in time Transparent disk 120 may have a horizontal axis. Transparent disk may be rotatable around the horizontal axis, i.e., a rotatable transparent disk, as described below.

The rotating of transparent disk 120 on its horizontal axis may further result in transparent disk 120 enhancing and/or facilitating the flow of fluid 110 through gap 30. In some examples, rotating transparent disk 120 may act as a viscous pump for fluid The viscous pumping action of transparent disk 120 may be configured to facilitate or enhance the movement of fluid 110 through gap 30, particularly when fluid 110 is a high density fluid, or a viscous fluid, or a fluid, like black ink, that may have a substantial concentration of solid particles, or fluid that is thick, flowing from inlet 60 to outlet 70 and through gap 30. Gap 30 may be, in some examples, too narrow for a fluid 110 that is of high density, or for fluid 110 with a high concentration of solid particles, or a thick fluid, to pass through unassisted, due to the width of gap 30.

Typically, the greater the viscosity of the fluid the more energy is typically necessary to enhance or facilitate the fluid to flow in a narrow gap.

In some examples, the viscous pump may be configured to act as a positive displacement rotary pump by moving fluid using principles of rotation. A vacuum created by the rotation of the pump may capture and draw in the liquid, e.g., fluid 110, through gap 30. The viscous pump may have a flow rate of between 20 and 900 cubic meters per second (m3/s). Typically, densitometer 100 is coupled to control unit 140. In some examples motor 130 is coupled to control unit 140.

Figure 1B:
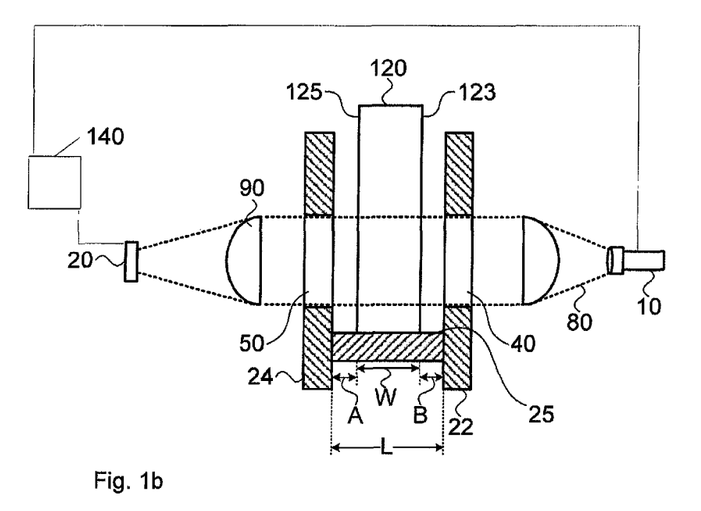
FIG. 1b is a further schematic illustration of the transparent disk configured to be placed in a gap between a light source and a receiver according to one example.

FIG. 1b is a schematic illustration of a transparent disk configured to be placed in a gap between a light source and a receiver.

Typically, transparent disk 120 has a width W. W may be between 1000 to 3000 microns. Transparent disk may serve to narrow the width of gap 30 that light beam 5 from light source 10 travels between window 40 and window 50. When transparent disk 120 is in gap 30, the intensity of light beam 5 may be attenuated (i.e., partially absorbed by fluid 110 present in gap 30) particularly when traveling along leg B between window 40 and surface 123 of transparent disk 120, and leg A between surface 125 of transparent disk 120 and window 50, but typically not when light beam 5 is traveling through transparent disk 120. Thus the effective sampling width L, typically the width of gap 30 between window 40 and window 50, for light beam 5 traveling from light source 10 through densitometer 100, may be effectively reduced to A+B, where A+B+W is equal or nearly equal to the width of gap 30.

This effective reducing of the sampling width L within gap 30 to A+B may provide for greater accuracy in determining the experimental optical density of fluid 110.

Figure 2A:
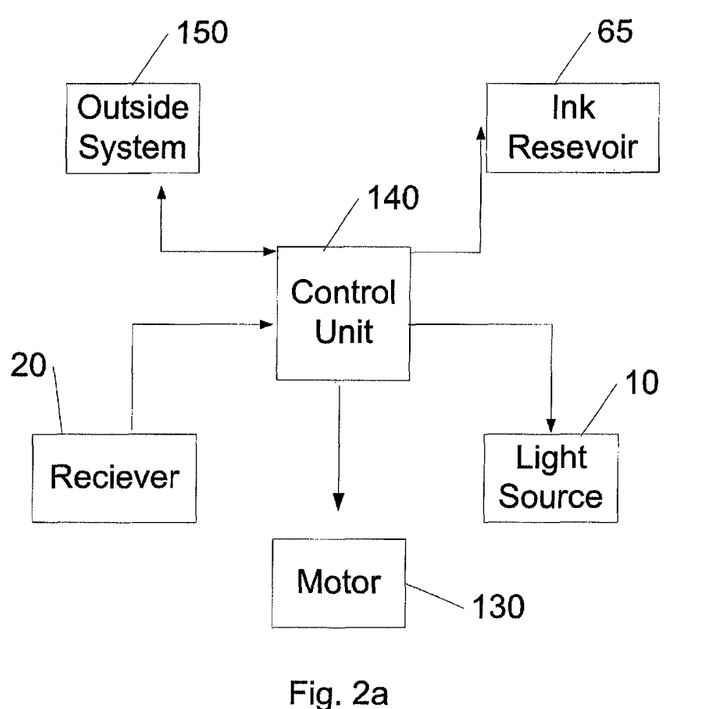
FIG. 2a is a schematic illustration relating to a control unit according to one example.

FIG. 2a is a schematic illustration of some of the interactions of control unit 140. For example, a control unit 140 is configured to determine, based on data regarding the traveling of light beam 5 across gap 30, an empirical optical density value for fluid 110. Control unit 140 may also control the rotation of transparent disk 120, typically via the driver, typically motor 130. Control unit 140, in some examples, may control the flow of fluid 110 from inlet 60 to outlet 70. In some examples, control unit controls the flow of fluid 110 via control over ink reservoir 65. Control unit 140 may extract data from receiver 20 from a sampled duration, e.g., sample data from densitometer 100 over a number of revolutions of transparent disk 120, e.g., between 120 and 9000 revolutions, in order to increase the accuracy of measurements of the optical density of fluid 110. In some examples, control unit 140 may also control light source 10. In some examples, in response to the assessed optical density of fluid 110, as measured by densitometer 100, control unit 140 may signal another system 150 to alter the makeup of fluid 110, such that the observed optical density of fluid 110 is changed to reflect the expected optical density. In some examples, control unit may signal another system in a printer apparatus to alter the makeup of ink such that the experimental optical density of the ink is changed. In some examples, control unit may signal another system in a printer apparatus to add solid pigment particles to an ink. In some examples, control unit may signal another system in a printer apparatus to add more fluid to an ink to dilute said ink due to a larger than expected concentration of solid pigment particles in the ink.

In some examples, control unit 140 may be coupled to hub and a motor, as described below with reference to FIG. 3b In some examples, control unit may be coupled to hub 340 and motor 350, as described below.

In some examples, control unit 140 may be connected to hub 410 and driver 400, as described below.

Figure 2B:
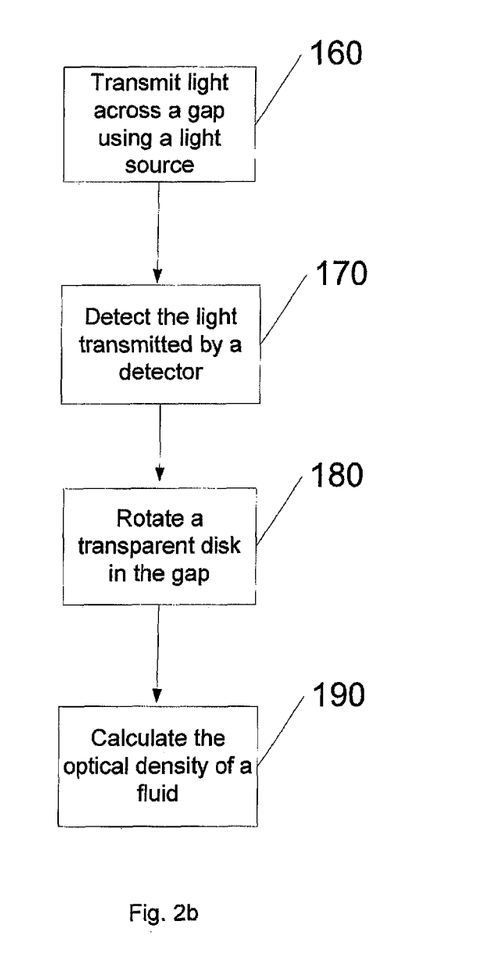
FIG. 2b is a flow diagram relating to the method of assessing the density of a fluid across a gap according to one example.

FIG. 2b is a flow diagram of a method for assessing the density of a fluid across a gap. Typically, a method to calculate the optical density of a fluid traveling through a gap includes transmitting light across the gap using a light source, as depicted by block 160. A detector, typically a photoelectric cell or another sensor known in the art, located opposite the light source, may be configured to detect the light transmitted from the light source, as depicted by block 170. A rotating transparent disk may be configured to occupy a portion of the gap and limit the volume of the gap that provides a pathway for fluid traveling though the gap, so as to provide a more precise measurement of the density of that fluid, as depicted by block 180. Rotating transparent disk 120 may facilitate or enhance the traveling of fluid 110 through gap 30.

In some examples, transparent disk 120 may rotate when an expected attenuation of light through fluid 110 is relatively high, e.g., having attenuation greater than about $10^{-4}$, to facilitate the passage of fluid 110 through gap 30. Typically, transparent disk 120 may be constantly rotating. In some examples, transparent disk 120 may only rotate when densitometer 100 is operating. In some examples, transparent disk may rotate during a majority of the time that a device containing densitometer is powered on Transparent disk 120 may not rotate, in some examples, when the expected attenuation of light through fluid 110 is relatively low, e.g., attenuated less than about $10^{-4}$.

The data resulting from the measurements of the attenuation of the light as it passes through the gap, and through the fluid, is then typically used by control unit 140 to calculate the optical density of the fluid as it passes through the gap, as depicted by block 190.

Figure 2C:
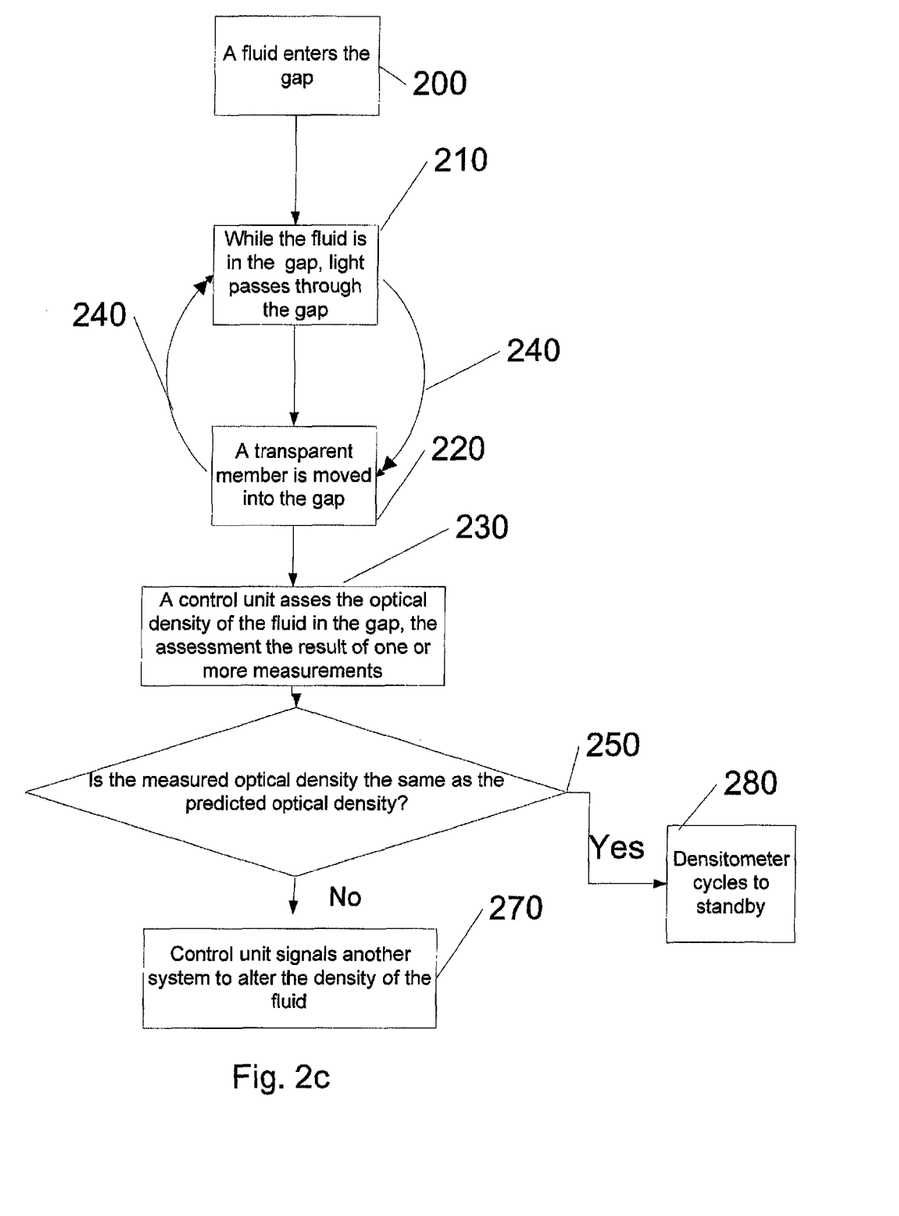
FIG. 2c is a flow diagram further relating to the method of assessing the density of a fluid across a gap according to one example.

FIG. 2c is a flow diagram of a method of assessing the density of a fluid across a gap.

In some examples, there may be different types of members within gap 30. In some examples, transparent disk 120, described above may be the member in gap 30. In some examples, other members, described below may be the member in gap 30. In some examples, transparent disk 120 or other members of different widths may occupy greater or lesser portions of gap 30, and, in some examples, may be introduced into gap 30 under some but not all conditions, as described below.

In some examples, fluid 110, typically ink, enters gap 30 through inlet 60, as represented by block 200.

Typically, fluid 110 may be directed to pass through gap 30. While passing through gap 30, light beam 5 from light source 10 may pass through collimating lens 80 and window 40, into gap 30, and through any fluid 110 in gap 30, passing through a transparent member moved into gap 30, through any remaining fluid 110 in gap 30, through window 50, through collecting lens 90 and to receiver 20, as represented by block 210.

The transparent member moved into or introduced into gap 30 may be configured to occupy a portion of the space within gap 30, as depicted by block 220 and as described below. The transparent member may occupy a portion of the space within gap 30, such that there is a reduction in the available volume within gap 30 for fluid 110 to pass through gap 30. This reduction of volume may limit the effective sampling width within gap 30, i.e., the area in gap 30 wherein light beam 5 passes through fluid 110 and not through the transparent member. This reduction in the effective sampling distance of light beam 5 may serve to allow a more precise measuring of high density fluids and provide a more accurate reading by densitometer 100.

In some examples, the transparent member is transparent disk 120 as described above with reference to FIG. 1, and as described below with reference to FIGS. 3a and 3b. Transparent disk 120 may be rotated around its horizontal axis within gap 30, the transparent disk configured to occupy a portion of gap 30.

In some examples, control unit 140 may choose one of a plurality of transparent disks to occupy a space within gap 30. Each one of the plurality of transparent disks, typically from a set of transparent disks, having a different width, wherein control unit 140 determines which transparent disk of a particular width to occupy a portion of gap 30. The determination of, the particular transparent disk of particular width may be based on the expected optical density of fluid 110 in gap 30.

In some examples, there may be no transparent disk in gap 30 while fluid 110 passes through gap 30.

In some examples, the transparent member is a transparent spacer 300 as described below with reference to FIG. 4. Typically, the transparent member is one of a plurality of transparent spacers 300; each of the plurality of transparent spacers may have a different width. Transparent spacer 300 may be introduced into gap 30. Typically, the transparent spacer does not rotate within gap 30.

The determination as to which particular transparent spacer of particular width should be introduced into the gap by control unit 140 may be based on the expected optical density of fluid 110 in gap 30.

In some examples, there may be no transparent spacer 300 in gap 30 while fluid 110 passes through gap 30. In some examples, transparent spacer may be configured to move into and out of gap 30. In some examples, gap 30 may be washed after transparent spacer 300 has been moved out of gap 30.

In some examples, the transparent member is a transparent spoke 330, as described below with reference to FIG. 5. Typically, the transparent spoke is one of a plurality of transparent spokes, each of the transparent spokes having a different width. One of the transparent spokes of a particular width may be introduced into gap 30. The determination by control unit 140 as to which particular transparent of spoke of particular width may be based on the expected optical density of fluid 110 in gap 30.

In some examples, there may be no transparent spoke 330 in gap 30 while fluid 110 passes through gap 30. In some examples, transparent spoke 330 may be configured to move into and out of gap 30. In some examples, gap 30 may be washed after transparent spoke 330 has been moved out of gap 30.

As depicted in block 230, control unit 140 assess the measured optical density of fluid 110 as determined by densitometer 100. This measurement may be the result of a collection of multiple iterations of light beam 5 passing through fluid 110, while the transparent member is in the gap. The multiple iterations are depicted by arrows 240.

In response to the assessed optical density of fluid 110, as measured by densitometer 100, control unit 140 may determine if the measured optical density the same as the predicted optical density, as depicted by diamond 250. If control unit determines that the measured optical density is sufficiently different than the predicted optical density then control unit 140 may signal another system 150, to alter the makeup of fluid 110, such that the experimental optical density of fluid 110 is changed, as depicted by block 270. In some examples, the optical density of fluid 110 is related to the concentration of solid particles in fluid 110. In some examples, control unit 140 determines that the measured optical density is close to the value, or equal to the value of the predicted optical density. Typically, control unit 140 may then send a signal to densitometer 100 to cycle to standby, and fluid 110 continues to travel through the pathway and out outlet 70, as depicted by block 280.

In some examples, once the density of the fluid has been altered, the densitometer measures the density of the altered fluid as it enters gap 30, as depicted by block 200. In some examples, the densitometer cycles to standby, and fluid 110 continues to travel through the pathway and out outlet 70, as depicted by block 280.

Figure 3A:
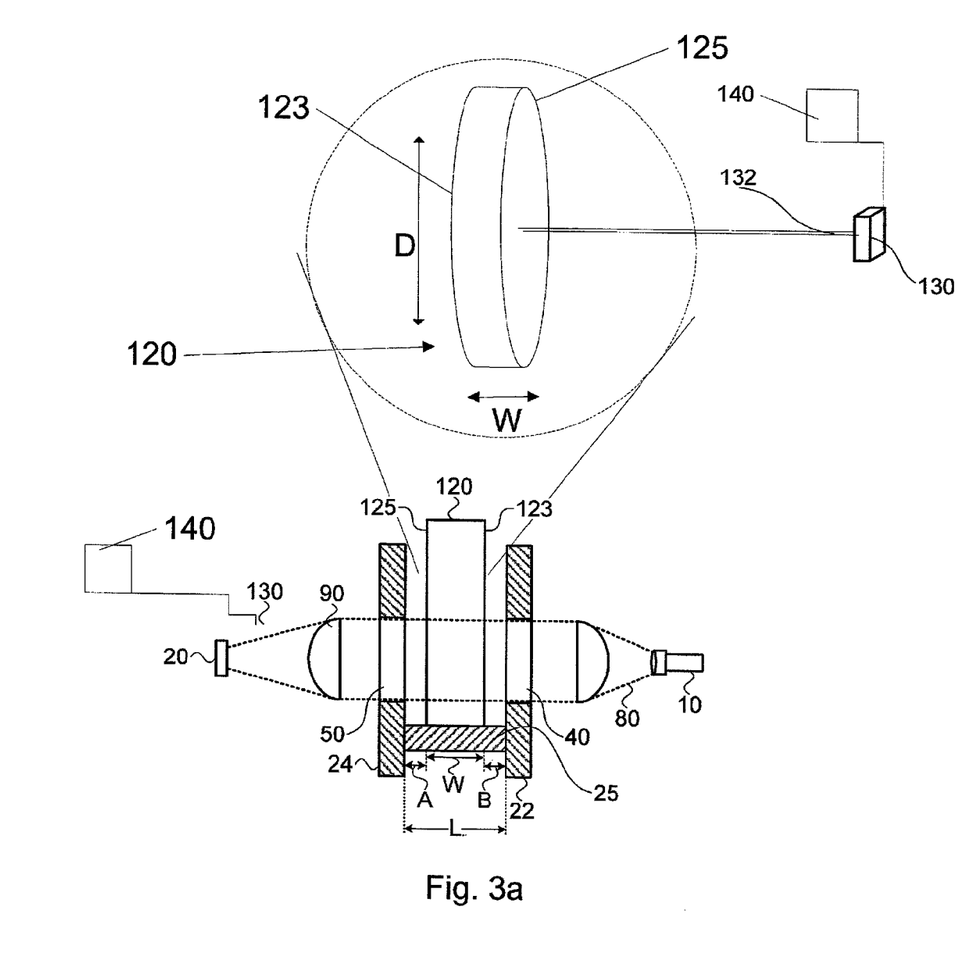
FIG. 3a is a schematic illustration of one or a plurality of transparent disks configured to be placed in a gap between a light source and a receiver according to one example.

FIG. 3a is a schematic illustration of an example of a densitometer with one or a plurality of transparent disks in the gap.

In some examples, there may be one, or a plurality of, transparent disks 120. Each transparent disk may be of a different width W as described above. Each transparent disk 120 of width W may be calibrated to be of sufficient width to sufficiently narrow the effective sampling width L of gap 30 for a particular fluid 110 with a given expected optical density.

Typically control unit 140 is configured to rotate transparent disk 120. Transparent disk 120 may be coupled to a driver, for example, a motor 130, the driver configured to rotate transparent disk 120 around its horizontal axis. The driver may be configured to be connected to the rotatable transparent disk 120 via connector 132. Transparent disk 120 may rotate around its horizontal axis as fluid 110 passes from inlet 60 to outlet 70. Motor 130, which may be one of the motors known in the art, is typically configured to rotate transparent disk 120 at between 120 to 4000 revolutions per minute (RPM).

FIG. 3a shows a cut-away of a fraction of transparent disk 120 within gap 30. In some examples, diameter D of transparent disk 120 is greater in magnitude than the height of gap 30, wherein only a fraction of transparent disk 120 is within gap 30 at any given point in time In some examples, diameter D of transparent disk 120 is substantially greater in magnitude than the height of gap 30. Typically, the coupling of motor 130 via connector 132 is outside, e.g., typically below, and in some examples, above gap 30, Typically, control unit 140 selects transparent disk 120 with particular width W. Transparent disk 120 with width W may be calibrated to be used with fluid 110 of an expected optical density as fluid 110 passes through gap 30. The selected transparent disk 120 with width W may be moved into gap 30 to narrow the effective sampling width L within gap 30, as described below, such that densitometer 100 can effectively measure the optical density of fluid 110. The one or a plurality of transparent disks may be connected to a hub 410, as described below.

Transparent disk 120 may be inserted or moved into the gap by means known in the art. In some examples, transparent disk 120 is inserted into gap by means of a hub as described below with reference to FIG. 3b.

Light beam 5 from light source 10 may pass through lens 80, window 40 and into gap 30 where fluid 110 of an expected density is configured to pass through in a pathway perpendicular, or nearly perpendicular to the pathway of, light from light source 10, from inlet 60.

Fluid 110 may pass through gap 30 in area of gap 30 of a width B. Typically, B may be the distance from window 40 to surface 123 of transparent disk 120 with width W.

Fluid 110 may also pass through gap 30, in an area of gap 30 of a width A. Typically, A may be the distance from surface 125 of transparent disk 120 with width W to window 50.

Typically, light beam 5 may continue to pass through transparent disk 120 through fluid 110 in gap 30 through window 50, through collecting lens 90 and to receiver 20.

Densitometer 100 may calculate the optical density of fluid 110 given the data from the transmission of light across the width of effective sampling width L of gap 30. Typically, densitometer 100 measures the optical density of fluid 110 passing through gap 30 with an effective sampling width L, where the effective sampling width L of gap 30 is narrowed to the equivalent, or near equivalent of A+B and where A+B may be less than width of gap 30 and where gap 30 may be equal to A+W+B.

Densitometer 100 may calculate numerous iterations of light transmission from light source 10 through fluid 110 to receiver 20. Control unit 140 may determine the measured optical density of fluid 110 from data provided by densitometer 100 over these multiple iterations.

Transparent disk 120 with width W may be connected to a driver, e.g., motor 130. Transparent disk 120 may further act as a viscous pump for fluid 110 as it passes from inlet 60 through gap 30 to outlet 70, as described heretofore with reference to FIG. 1.

Control unit 140 may send a signal to alter the optical density of fluid 110, given the measured density of fluid 110 by densitometer 100. In some applications, the optical density of fluid 110 is related to the concentration of solid particles in fluid 110. The optical density of fluid 110 may be altered by changing the concentration of solid particles in fluid 110.

In some examples, transparent disk 120 of width W is not inserted into gap 30 for measurements by densitometer 100. Typically, if fluid 110 has an expected low light absorption, i.e., a low optical density, then control unit 140 will not insert a transparent disk into gap 30. In some examples, yellow ink may have low light absorption.

Typically, while transparent disk 120 is not within gap 30, gap 30 is configured to allow fluid 110 to pass without obstacles through gap 30 toward outlet 70. In some examples, if transparent disk 120 is removed from gap 30, gap 30 is washed.

Figure 3B:
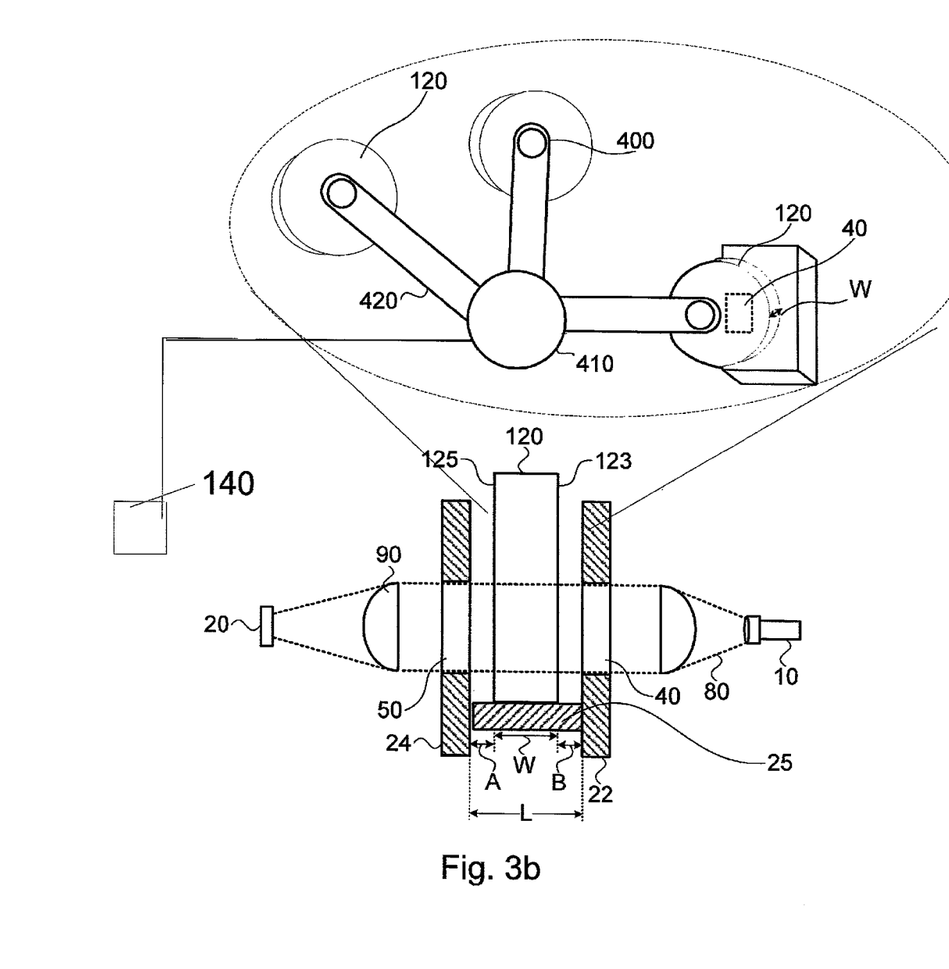
FIG. 3b is a further schematic illustration of one or a plurality of transparent disks configured to be placed in a gap between a light source and a receiver according to one example.

FIG. 3b is a schematic illustration of an example incorporating a set of one or a plurality of replaceable transparent disks 120, the set of one or a plurality of replaceable transparent disks pivoted into another perspective for illustrative purposes.

In some examples, one, or a plurality, of transparent disks 120 are connected to one, or a plurality of drivers 400. Transparent disk 120 is typically part of a set of replaceable transparent disks that may have different widths. Typically, these widths, W, range from 1000 to 3000 microns.

Driver 400 may be a motor, or may be connected to a motor, or other driver devices, as are known in the art. Driver 400 is connected to a central hub 410 by way of a connector 420.

Connector 420 may be a rigid material. In some examples, connector 420 is a flexible material.

Driver 400, typically outside gap 30, is configured to rotate transparent disk, 120, such that a rotating fractional portion of transparent disk 120 is rotating within gap 30, and wherein a larger fractional portion coupled to driver 400 is outside of gap 30, similar to as described earlier with reference to FIG. 3a. The rotation of transparent disk is further described above with reference to FIG. 1, with exceptions noted.

In response to a signal from control unit 140, hub 410 may be configured to introduce a transparent disk 120 into gap 30. Control unit 140 may, in response to information regarding the expected optical density of fluid 110 entering gap 30, send a signal to introduce a transparent disk 120 with width W into gap 30. Typically, the transparent disk is part of a set of replaceable transparent disks, in some examples, a set of replaceable transparent disks of different widths. The transparent disk selected by control unit 140 to be introduced into gap 30 may be typically calibrated to sufficiently narrow the distance that light beam 5 travels through fluid 110 within gap 30 such that the optical density of fluid 110 can be effectively measured by densitometer 100.

Typically, a transparent disk is introduced into gap 30 by rotating hub 410 until the appropriate transparent disk is in gap 30. FIG. 3b shows a cut-away of the diameter D of transparent disk 120, wherein a fraction of the transparent disk may be in gap 30, typically transparent disk is larger than the volume of gap 30.

In some examples, when the expected optical density of a fluid is such that the attenuation of light by fluid 110 as it passes through gap 30 is not expected, to sufficiently affect the accuracy of the measurement of the optical density of the fluid, control unit 140 will not introduce or move in a transparent disk 120 into gap 30, and fluid 110 may be able to flow through gap 30 without any obstacles.

In some examples, a first transparent disk 120 with a particular width may be replaceable with one or a plurality of different transparent disks 120 with different particular widths. Typically, in response to an expected optical density of fluid 110, control unit 140 may send a signal to remove a first transparent disk 120 currently in gap 30 and replace it with at least a second transparent disk 120 with a different width, the width of the at least second transparent disk 120 may be calibrated to enhance the measurements of densitometer 120 by changing the current effective sampling width L of gap 30.

In some examples, control unit 140 may be configured to control the revolutions per minute of the particular transparent disk with width W while the transparent disk is in the gap, the rotation as described above.

Figure 4:
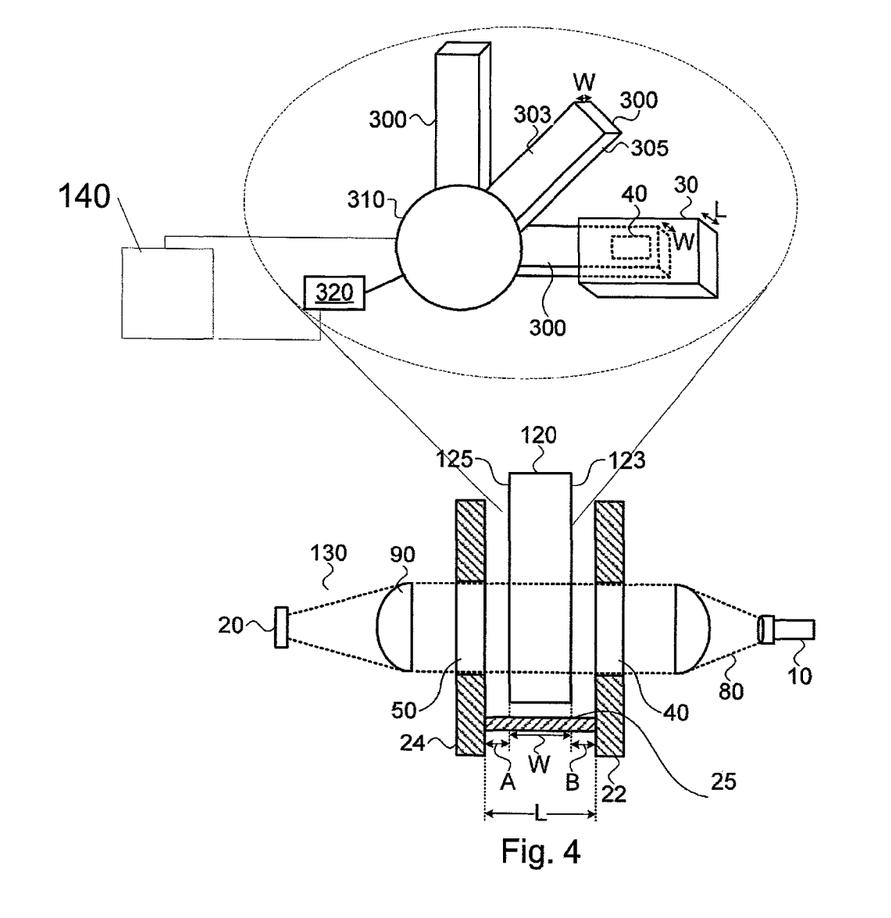
FIG. 4 is a schematic illustration of one or a plurality of transparent spacers configured to be placed in a gap between a light source and a receiver according to one example; and, FIG. 5 is a schematic illustration of one or a plurality of transparent spokes configured to be placed in a gap between a light source and a receiver according to one example.

FIG. 4 is a schematic illustration of an example incorporating a removable transparent spacer, the transparent spacers pivoted into another perspective for illustrative purposes.

In some examples, a removable transparent spacer 300 may be introduced into or moved out of gap 30. Transparent spacer 300 is typically made of transparent plastic but can be made from any transparent material known in the art. Spacer 300 may be typically transparent to light beam 5. Transparent spacers are typically from 1000 to 3000 microns wide.

In some examples, there is more than one transparent spacers 300, e.g., a set of transparent spacers. Each transparent spacer may be coupled to a hub 310. Typically, hub 310 is connected to a driver. The driver may be motor 320, or may be connected to motor 320. Motor 320 is typically any motor known in the art. Control unit 140 may be coupled to motor 320 and hub 310.

In response to a signal from control unit 140, hub 310 maybe configured to introduce a transparent spacer 300 into gap 30. Transparent spacers 300 may have different widths, W. Typically these widths range from 200 to 4000 microns.

In some examples, multiple transparent spacers are connected to hub 310. Control unit 140 may, in response to information regarding the expected optical density of fluid 110 entering gap 30, introduce transparent spacer 300 with width W into gap 30. Typically, the transparent spacer selected by control unit 140 to be moved into gap 30 is calibrated to sufficiently narrow the effective sampling width L of gap 30, given the expected optical density of fluid 110, such that the optical density of fluid 110 can be effectively measured by densitometer 100 as light beam 5 passes through gap 30.

In some examples, for some expected optical densities, particularly when the expected optical density of a fluid is such that the attenuation of light by fluid 110 as it passes through gap 30 is not expected to sufficiently affect the accuracy of the measurement of the optical density of the fluid, control unit 140 will not introduce a transparent spacer 300 into gap 30.

Different transparent spacers are typically attached to hub 310; typically only one transparent spacer at a time is moved into gap 30 by the driver or motor 320.

In some examples, fluid 110 is unable to sufficiently pass through gap 30 while transparent spacer 300 is also in gap 30. In some examples, transparent spacer 300 is moved into and out of gap 30, at a speed that is typically dependent on the viscosity or thickness of the fluid. In some examples, gap 30 is washed each time transparent spacer is moved out of gap 30.

In some examples, light beam 5 from light source 10 passes through collimating lens 80, through window 40, through gap 30, any fluid 110 in gap 30, and to surface 303 of transparent spacer 300. Light beam 5 then travels through transparent spacer 300, through surface 305 of transparent spacer 300, through the remainder of gap 30, and through any fluid 110 in the remainder of gap 30, through window 50, through collecting lens 90 and to receiver 20.

The distance that light beam 5 travels between window 40 and surface 303 is equal to B. The distance that light beam 5 travels between surface 305 and window 50 is equal to A. Typically A+W+B will be the equivalent or near equivalent of the width of gap 30. Typically, A+B may be the equivalent or near equivalent of the narrowed effective sampling width L of gap 30 for densitometer 100 when spacer 300 is within gap 30.

Typically, while transparent spacer 300 is within gap 30, densitometer 100 may be configured to measure the optical density of fluid 110 passing into gap 30. In some examples, control unit 140 analyzes several iterations of fluid 110 flowing into gap 30, while transparent spacer 300 may be moving into and out of gap 30, to determine the observed optical density of fluid 110.

Typically, control unit 140 will analyze multiple data points from densitometer 100, each data point calculated when transparent spacer 300 is in gap 30. Typically, fluid 110 is unable to pass efficiently through gap 30 while transparent spacer 300 is within gap 30.

Typically, while transparent spacer 300 is not within gap 30, gap 30 is configured to allow fluid 110 to pass uninhibitedly through gap 30 toward outlet 70.

In some examples, transparent spacer 300 is not inserted into gap 30 for measurements by densitometer 100. Typically, if fluid 110 has a sufficiently low expected light absorption, as may be determined, in some examples from experimental data, then control unit 140 will not insert a transparent spacer 300 into gap 30.

In some examples, transparent spacer 300 may also be configured to include an optical, density calibration target 315 for densitometer 100. In some examples, a transparent spacer containing a calibration target may be moved into gap 30 for densitometer 100 to calibrate itself against a calibration target, typically a colored glass with a known optical density and absorption coefficient.

Figure 5:
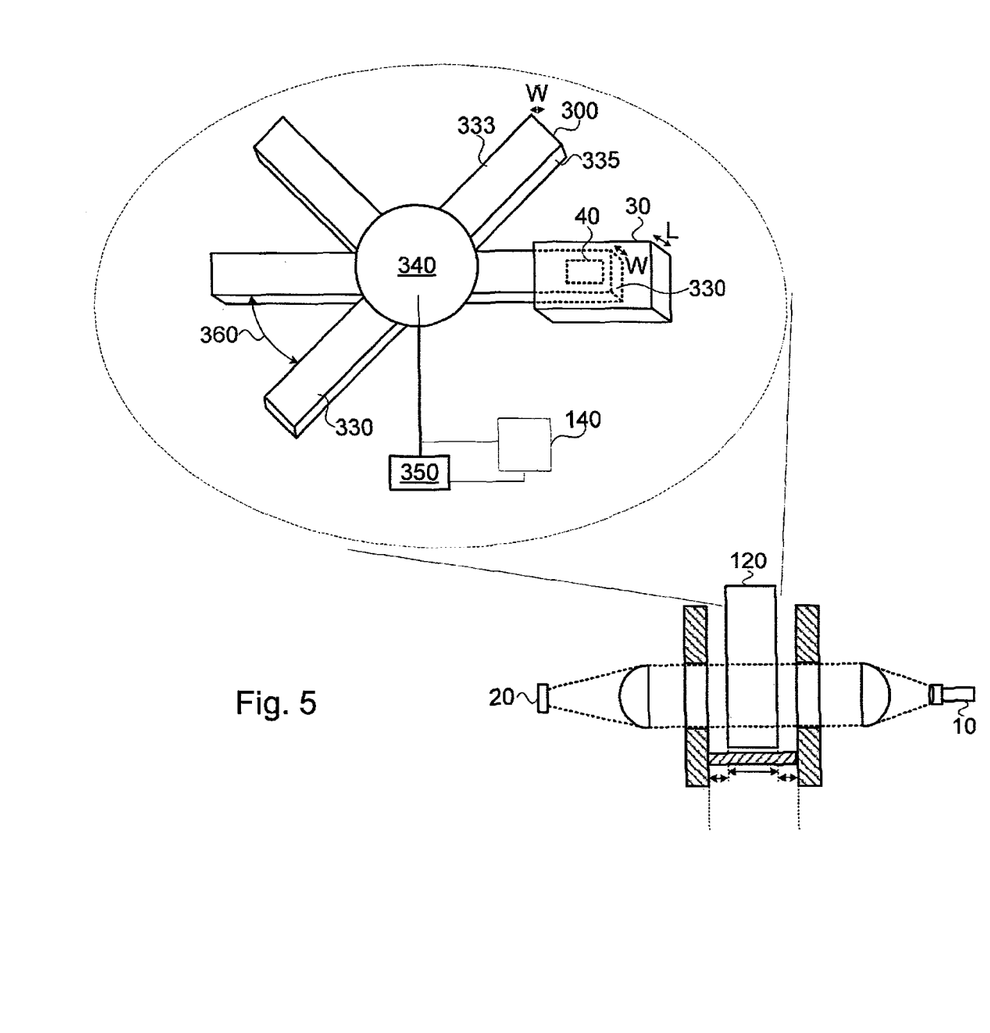

FIG. 5 is a schematic illustration of an example wherein transparent spokes may be inserted into gap 30, the transparent spokes pivoted into another perspective for illustrative purposes. Typically, transparent spoke 330 is connected to a hub 340. Typically, there may be one ore more transparent spokes 330 connected to hub 340.

Hub 340 is typically connected to a driver; the driver may be motor 350, motor 350 being any known motor in the art. Hub 340 is typically configured to rotate in response to a signal from control unit 140.

In some examples, each spoke 330 on hub 340 has a particular width W. The width W may be typically calibrated to fit within gap 30. Each spoke 330 with width W may also be particularly calibrated to fit into gap 30 to measure the particular optical density of fluid 110 with a particular expected optical density, or a particular range of expected optical densities. Typically, each spoke 330 may be from 1000 to 3000 microns wide. Typically there are empty spaces 360 between each of the transparent spokes connected to hub 340.

In some examples, in response to a signal from control unit 140, motor 350 rotates hub 340 such that a particular spoke 330 of a particular width W is rotated into gap 30. In some examples, in response to a signal from control unit 140, motor 350 rotates hub 340 such that space 360 is in gap 30.

Typically, control unit 140 may send a signal to rotate hub 340 in response to the entering of fluid 110 into inlet 60 toward gap 30. Fluid 110 may have a predicted optical density. In order to sufficiently narrow the effective sampling width L of gap 30 such that densitometer 100 may accurately measure the optical density of fluid 110, control unit 140 may signal for a particular spoke 330 of a particular width W to move into gap 30.

In some examples, while spoke 330 is in gap 30, light source 10 will send light beam 5 through collimating lens 80, through window 40, across gap 30, through fluid 110, to surface 333 of transparent spoke 330, the distance from window 40 to surface 333 of transparent spoke 330 equal to B. Light beam 5 typically travels through transparent spoke 330 without attenuation. Light beam 5 may continue to travel through spoke 330, through surface 335 of transparent spoke 330, through the remainder of gap 30 and typically any fluid 110 in the remainder of gap 30, through window 50, through collecting lens 90 and to receiver 20. The distance between surface 335 of transparent spoke 330 and window 50 is equal to A.

Typically the width of gap 30 may be the equivalent or a near equivalent of A+W+B, with the narrowed effective sampling width for densitometer 100 the equivalent, or near equivalent of A+B.

Typically, control unit will analyze multiple data points from densitometer 100, each data point typically representing a time period when spoke 330 is in gap 30. Typically fluid 110 is unable to pass sufficiently through gap 30 while spoke 330 is within gap 30. In some examples, transparent spoke 330 may move into and out of gap 30.

In some examples, transparent spoke 330 is not inserted into gap 30 for measurements made by densitometer 100. Typically, if experimental data suggest that fluid 110 has an expected low light absorption, then control unit 140 may not insert a transparent spoke 330 into gap 30. Typically, one of the spaces 360 between spokes 330 may be inside gap 30. The space 360 between spokes 330 configured to allow fluid 110 to pass uninhibitedly through gap 30 toward outlet 70.

In some examples, transparent spoke 330 may also be configured to include an optical density calibration target, similar to calibration target 315 referenced above, for densitometer 100. In some examples, a transparent spoke 330 containing a calibration target may be moved into gap 30 for densitometer 100 to calibrate itself against a colored element with a known optical density and absorption coefficient.

In some examples, after transparent spoke 330 is removed from gap 30, gap 30 is washed.

Features of various examples discussed herein may be used with other embodiments discussed herein. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. An apparatus to calculate an optical density of a fluid traveling through a gap having a width, comprising:
   a light source configured to transmit light across the gap;
   a detector, opposite the light source, configured to detect light transmitted from the light source, across the width of the gap for calculating the optical density of the fluid;
   at least one rotatable transparent disk configured to occupy a portion of the width of the gap between the light source and the detector so as to reduce available width of the gap for the fluid traveling through the gap, and configured to enhance a flow of the fluid through the gap to compensate for a reduction of the available width of the gap limiting the flow of the fluid through the gap; and,
   a driver to rotate the rotatable transparent disk.

2. The apparatus of claim 1, wherein said at least one transparent disk comprises a set of replaceable transparent disks of different widths.

3. The apparatus of claim 1, linked to an ink reservoir of a printer, wherein the fluid is the ink.

4. The apparatus of claim 1, wherein the apparatus is further configured to send a signal to alter the fluid after calculating the optical density of the fluid.

5. A method to calculate an optical density of a fluid traveling through a gap, comprising:
   transmitting light across the gap using a light source;
   detecting the light transmitted from the light source, across the gap by a detector located opposite the light source;
   rotating a transparent disk configured to occupy a portion of the gap to reduce available width of the gap for the flow traveling through the gap, and configured to enhance a flow of the flow of the fluid through the gap to compensate for a reduction of the available width of the gap limiting the flow of the fluid through the gap; and
   calculating the optical density of the fluid as it passes through the gap.

6. The method of claim 5, wherein the calculating of the optical density of the fluid as it passes through the gap comprises detecting the light over a sampled duration of one or a plurality of rotations of the transparent disk.

7. The method of claim 5, wherein the transparent disk is replaceable with another transparent disk, and is a part of a set of replaceable transparent disks of different widths.

8. An apparatus to calculate an optical density of a fluid traveling through a narrow gap having a width, comprising:
a light source configured to transmit light across the gap;
a detector, opposite the light source, configured to detect light transmitted from the light source, across the gap for calculating the optical density of the fluid; and,
at least one transparent member, the transparent member configured to be moved into and out of the gap, between the light source and the detector so as to modify an effective sampling width of the gap,
wherein the transparent member is rotatable within the gap to enhance a flow of the fluid through the gap to compensate for a reduction of the effective sampling width of the gap limiting the flow of the fluid through the gap.

9. The apparatus of claim 8, wherein the transparent member is configured to be in the narrow gap when calculating the optical density of a fluid, and moved out of the narrow gap when fluid travels through the narrow gap.

10. The apparatus of claim 8, wherein the transparent member is configured to be moved out of the gap when the fluid is predicted to be of a low optical density.

11. The apparatus of claim 8, wherein the transparent member comprises a calibration target with a known optical density.

12. The apparatus of claim 8, linked to an ink reservoir of a printer, wherein the fluid is the ink.

13. The apparatus of claim 8, wherein the apparatus is further configured to send a signal to alter the fluid after calculating the optical density of the fluid.

14. The apparatus of claim 1, wherein the rotatable transparent disk acts as a viscous pump to enhance the flow of the fluid through the gap.

15. The apparatus of claim 1, wherein the driver is to:
determining an expected attenuation of the light through the fluid;
when the expected attenuation is greater than a threshold, rotate the rotatable transparent disk; and
when the expected attenuation is less than the threshold, not rotate the rotatable transparent disk.

16. The apparatus of claim 1, wherein the driver is to rotate the rotatable transparent disk constantly regardless of whether the light source and the detector are operating.

17. The apparatus of claim 1, wherein the driver is to rotate the rotatable transparent disk just when the light source and the detector are operating.

* * * * *